United States Patent [19]

Leupold et al.

[11] Patent Number: 5,490,936
[45] Date of Patent: Feb. 13, 1996

[54] PROCESS FOR CATALYST RECOVERY

[75] Inventors: Ernst I. Leupold, Neu-Anspach; Wolf-Dietmar Kaufmann, Kronberg; Bernd Laugwitz, Kelkheim/Taunus; Günther Duchatsch, Liederbach; Ulrich Meyer-Blumenroth, Idstein, all of Germany

[73] Assignee: Hoechst Aktiengesellschaft, Germany

[21] Appl. No.: 224,066

[22] Filed: Apr. 7, 1994

Related U.S. Application Data

[63] Continuation of Ser. No. 937,889, Nov. 23, 1992, abandoned.

[30] Foreign Application Priority Data

Apr. 14, 1990 [DE] Germany ............................ 40 12 128.3

[51] Int. Cl.$^6$ .................................................. B01D 61/16
[52] U.S. Cl. .......................... 210/636; 210/639; 210/651
[58] Field of Search ............................ 208/308; 210/636, 210/639, 651, 652

[56] References Cited

U.S. PATENT DOCUMENTS

| | | |
|---|---|---|
| 2,757,800 | 8/1956 | Kucera . |
| 4,756,821 | 7/1988 | Giuliani et al. ...................... 208/308 X |
| 4,861,471 | 8/1989 | Nakao et al. . |
| 5,128,107 | 7/1992 | Katoh et al. ...................... 210/497.4 X |
| 5,230,804 | 7/1993 | Leupold et al. ...................... 210/653 X |

FOREIGN PATENT DOCUMENTS

| | | |
|---|---|---|
| 2936123 | 4/1981 | Germany . |
| 0645608 | 10/1984 | Switzerland . |

OTHER PUBLICATIONS

*Ullmann's Encyclopedia of Industrial Chemistry*, Fifth Edition, vol. B2, Editor: Elvers et al, 1988, pp. 10–53 and 10–54.

*Primary Examiner*—Frank Spear
*Attorney, Agent, or Firm*—Connolly & Hutz

[57] ABSTRACT

Process for the recovery of catalyst in the production of ether carboxylic acids by catalytic oxidation with a suspended ether catalyst in which the reaction mixture is subjected to cross-flow filtration.

11 Claims, 1 Drawing Sheet

CROSS-FLOW FILTRATION
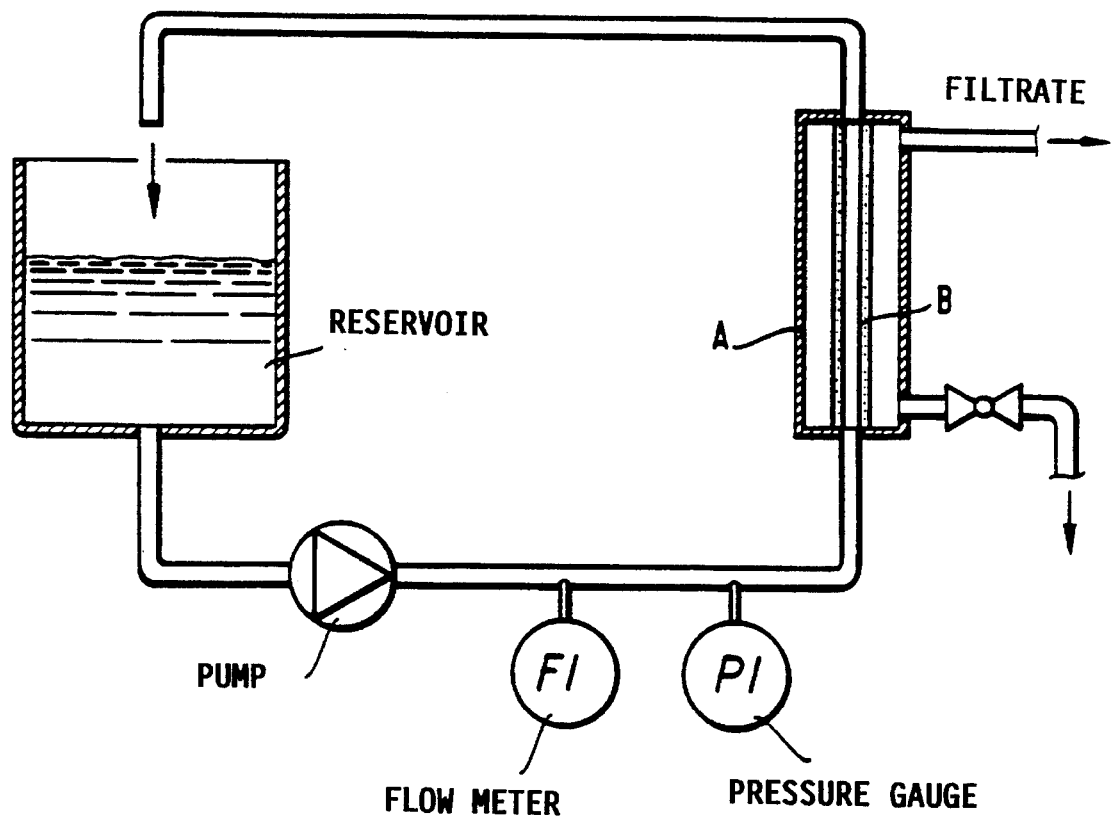

PROCESS FOR CATALYST RECOVERY

This application is a continuation of application Ser. No. 07/937,889 filed on Nov. 23, 1992, now abandoned.

The present invention relates to a process for the recovery of catalyst in the preparation of ether-carboxylic acids by catalytic oxidation of the corresponding ether alcohols with oxygen on suspended noble metal catalysts.

The catalytic oxidation of ether alcohols according to the general equation

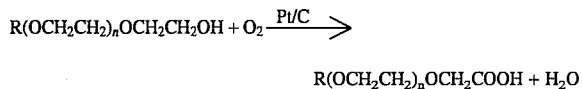

$$R(OCH_2CH_2)_nOCH_2CH_2OH + O_2 \xrightarrow{Pt/C}$$
$$R(OCH_2CH_2)_nOCH_2COOH + H_2O$$

has long been known and is described for example in German Patent 2,936,123 and European Patent 206,054. However, as the molar mass of the radical R increases, the separation and thus the complete recovery and recycling of the noble metal catalyst becomes problematic. Thus in German Patent 3,446,561, on page 4, a laborious four-stage method is described to restrict the losses of noble metal. An essential processing disadvantage of this procedure lies in the fact that the reaction mixture, prior to the filtration, is diluted with 1–10 times the amount of acetone, which must then be removed again by distillation, purified and recycled. The noble metal contents of 1–4 ppm, which can ultimately be obtained in the product, are also relatively high and lead to a gradual decrease in the activity of the catalyst. Overall, this entails a serious economic disadvantage.

The object was therefore to develop an industrially and economically acceptable process for catalyst recovery.

The subject of the present invention is a process for the recovery of catalyst in the preparation of ether-carboxylic acids by catalytic oxidation using a suspended catalyst, characterized in that the reaction mixture is subjected to a cross-flow filtration.

Preferred ether-carboxylic acids are those of the formula

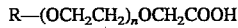

$$R-(OCH_2CH_2)_nOCH_2COOH$$

in which R is a linear or branched alkyl radical of 1 to about 24 carbon atoms, an aryl radical, such as for example a phenyl, naphthyl or biphenyl radical, additionally an alkyl($C_1$–$C_{24}$)aryl radical, the aryl radical being for example a phenyl, naphthyl or biphenyl radical, or an arylalkyl radical, for example a benzyl radical, and n is a number from 0 to about 24. The abovementioned aryl radicals can be substituted.

In cross-flow filtration, the catalyst-containing reaction mixture is pumped at a high overflow velocity tangentially to the membrane surface through the filter element, the filtrate being withdrawn perpendicular to the direction of flow through the membrane layer, as described in detail in ULLMANN's Encyclopedia of Industrial Chemistry, 5th Edition, Vol. B2, p. 10–54.

The drawing FIGURE shows the cross-flow filtration apparatus.

Tube-shaped filter elements having a membrane layer on the inner side of the tubes are particularly suitable. Preferred membrane and support material is α-$Al_2O_3$ and $ZrO_2$; however, plastic and carbon elements can also be used. Membrane and support can be composed of different materials. The necessary pore sizes are expediently in the ultrafiltration range, for example between about 1 and about 200 nm. A suitable apparatus is described in the example.

The cross-flow filtration according to the invention can be performed at temperatures from about 20° to about 150° C.

It has proved to be advantageous to carry out the filtration at temperatures from about 50° to about 100° C., in particular at temperatures from about 60° to about 80° C.

A pressure drop must of course prevail between the front side and the rear side of the membrane, so that the reaction solution can be moved through.

A solubilizer used in the oxidation can facilitate filtration. Solubilizers without hydroxyl groups are suitable. Glycol ethers without hydroxyl groups are particularly suitable, in particular diethylene glycol dimethyl ether.

A brief hydrogen treatment after the oxidation is completed at the reaction temperature (about 50° to about 100° C.) has proved to be advantageous, to precipitate any dissolved and colloidal noble metal traces, so that filter elements with somewhat larger pores can be used. Apart from hydrogen, formaldehyde, for example, can also be used as reducing agent.

Surprisingly, the problems of filtration (blockage, losses of noble metals) are solved by the process according to the invention without the need for expensive measures, such as for example dilution with a solvent.

The example below serves to illustrate the process according to the invention without restricting it thereto.

Example

A reaction solution from the catalytic oxidation, comprising 25% by weight of ether-carboxylic acids of the formula R—(OCH$_2$CH$_2$)$_n$OCH$_2$COOH having linear alkyl groups R having a distribution of $C_{12}$ to $C_{14}$ and a mean value of n=4 and also 45% by weight of diethylene glycol dimethyl ether, 25% by weight of water and 5% by weight of a suspended commercial catalyst (5% by weight of platinum on activated charcoal) is treated for 30 minutes at 70° C. with hydrogen in a bubble column and then subjected to a cross-flow filtration.

The filter element is composed of a $ZrO_2$ tube (diameter: 7 mm, length: 250 mm), the inner side of which is composed of a membrane layer having pore sizes of 35 nm ($10^{-9}$ m). An apparatus is used, which corresponds to the accompanying drawing. The reaction solution is pumped through the filter element (B) situated in a housing (A) at a linear flow velocity of 5 m/s. A pressure $P_1$ of 3 bar is established at a temperature of 70° C. A filtrate flow of 2.5 l/h is obtained. The catalyst is concentrated to a solids content of approximately 30% by weight; this concentrate is returned to the catalytic oxidation.

After separation of the diglycol dimethyl ether and water from the filtrate by distillation, the mixture of ether-carboxylic acids is obtained as a clear, pale product having a residual quantity of platinum of less than 0.5 ppm.

Comparison Example

The reaction solution described in the above example is repeatedly filtered on a suction filter with inserted filter paper (for quantitative analysis). The filter paper must be changed frequently because of blockage. A cloudy filtrate is obtained, which after work-up according to the example yields a dark, cloudy product having a platinum content of 36 ppm.

We claim:

1. Process for the recovery of catalyst in the preparation of ether-carboxylic acids by catalytic oxidation using a suspended catalyst, characterized in that the reaction mixture is treated with hydrogen and subjected to a cross-flow filtration in the presence of a solubilizer and the filtration is carried out at temperatures from about 20° to 150° C., and producing a resulting concentration of the catalyst in the filtrate of less than 0.5 ppm.

2. Process according to claim 1, characterized in that the ether-carboxylic acids are those of the formula $$R-(OCH_2CH_2)_nOCH_2COOH$$

in which R is a linear or branched alkyl radical having 1 to about 24 carbon atoms, an aryl, alkylaryl or arylalkyl radical unsubstituted or substituted at the aromatic nucleus and n is a number from 0 to about 24.

3. Process according to claim 1, characterized in that the filter element in the cross-flow filtration is composed of ceramic material and/or carbon.

4. Process according to claim 1, characterized in that the filter element in the cross-flow filtration is composed of $ZrO_2$ and/or $\alpha\text{-}Al_2O_3$.

5. Process according to claim 1, characterized in that the filtration is carried out at temperatures from about 60° to about 80° C.

6. Process according to claim 1, characterized in that the cross-flow filtration is performed in the presence of a solubilizer without hydroxyl groups.

7. Process according to claim 1, characterized in that the cross-flow filtration is performed in the presence of a glycol ether without hydroxyl groups.

8. Process according to claim 1, characterized in that the cross-flow filtration is performed in the presence of diethylene glycol dimethyl ether.

9. Process according to claim 1, characterized in that the reaction mixture, prior to the cross-flow filtration, is treated with hydrogen at temperatures from about 50° to about 100° C.

10. Process according to claim 1, characterized in that the reaction mixture is treated with a reducing agent.

11. The process of 10 wherein the reducing agent is hydrogen or formaldehyde.

\* \* \* \* \*